United States Patent
Lim et al.

(10) Patent No.: US 7,650,191 B1
(45) Date of Patent: Jan. 19, 2010

(54) IMPLANTABLE MEDICAL DEVICE HAVING A HEADER WITH AN INTEGRATED TELEMETRY COIL

(75) Inventors: Wisit Lim, Palmdale, CA (US); Narendra Nayak, Santa Clarita, CA (US); Pankaj Sunkeri, Burbank, CA (US)

(73) Assignee: Pacesetter, Inc., Sylmar, CA (US)

( * ) Notice: Subject to any disclaimer, the term of this patent is extended or adjusted under 35 U.S.C. 154(b) by 550 days.

(21) Appl. No.: 11/623,394

(22) Filed: Jan. 16, 2007

(51) Int. Cl.
*A61N 1/372* (2006.01)

(52) U.S. Cl. ........................................ 607/60
(58) Field of Classification Search ............... 607/32, 607/60
See application file for complete search history.

(56) References Cited

U.S. PATENT DOCUMENTS

| 5,342,408 | A | 8/1994 | deCoriolis et al. |
| 5,413,595 | A | 5/1995 | Stutz, Jr. |
| 5,562,713 | A | 10/1996 | Silvian |
| 5,951,595 | A | 9/1999 | Moberg et al. |
| 6,192,277 | B1 | 2/2001 | Lim et al. |
| 6,240,317 | B1 | 5/2001 | Villaseca et al. |
| 6,328,699 | B1 | 12/2001 | Eigler et al. |
| 6,428,368 | B1 | 8/2002 | Hawkins et al. |
| 6,567,703 | B1 * | 5/2003 | Thompson et al. ............ 607/60 |
| 6,809,701 | B2 | 10/2004 | Adundson et al. |
| 6,970,742 | B2 | 11/2005 | Mann et al. |
| 6,984,145 | B1 | 1/2006 | Lim |
| 7,103,413 | B2 | 9/2006 | Swanson et al. |
| 7,115,095 | B2 | 10/2006 | Eigler et al. |
| 7,137,953 | B2 | 11/2006 | Eigler et al. |
| 7,317,946 | B2 * | 1/2008 | Twetan et al. ................. 607/60 |
| 2003/0135246 | A1 * | 7/2003 | Mass et al. .................... 607/60 |
| 2004/0127960 | A1 * | 7/2004 | Mass et al. .................... 607/60 |
| 2004/0176811 | A1 | 9/2004 | Van Arx et al. |
| 2004/0215280 | A1 | 10/2004 | Dublin et al. |
| 2005/0134520 | A1 | 6/2005 | Rawat et al. |
| 2005/0203584 | A1 * | 9/2005 | Twetan et al. ................. 607/36 |
| 2008/0039898 | A1 * | 2/2008 | Lim et al. ..................... 607/32 |

FOREIGN PATENT DOCUMENTS

WO  WO 2005/115540 A1 * 12/2005

* cited by examiner

*Primary Examiner*—Carl H Layno
*Assistant Examiner*—Yun Haeng Lee

(57) ABSTRACT

An implantable medical device comprises a hermetically sealed casing enclosing electrical stimulation and/or sensing circuitry. A header on the casing comprises a longitudinal receptacle for receiving the electrical connector assembly of an electrical medical lead that senses cardiac blood pressure. The receptacle has electrical contacts engageable by corresponding electrical terminals on the connector assembly. A telemetry circuit assembly, mounted vertically within the confines of the header adjacent to the receptacle, comprises a winding having ends connected across the electrical contacts of the receptacle.

15 Claims, 6 Drawing Sheets

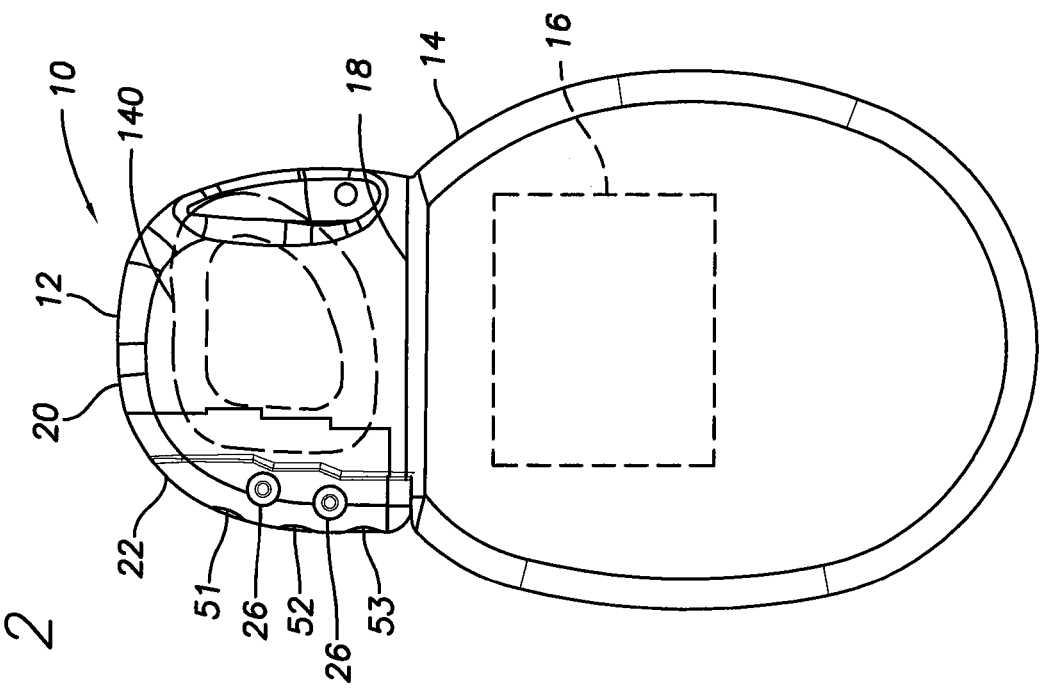
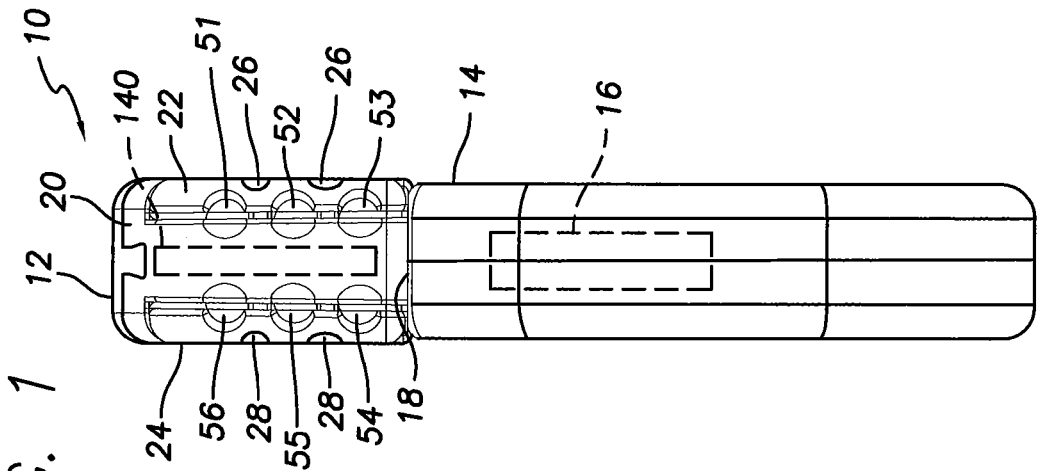

IMPLANTABLE MEDICAL DEVICE HAVING A HEADER WITH AN INTEGRATED TELEMETRY COIL

FIELD OF THE INVENTION

The present invention relates generally to implantable medical devices such as pacemakers or implantable cardioverter/defibrillators (ICDs) and particularly to a header for such devices that incorporates a telemetry coil permitting communication of signals by way of an electromagnetic energy link between the implantable medical device and an external system such as a handheld interrogation system.

BACKGROUND OF THE INVENTION

Cardiac pacemakers and other implantable stimulation devices such as cardioverters and defibrillators, are hermetically sealed within a housing or casing (sometimes also referred to as a "can") to isolate the electronic circuits contained within the device from the body environment. Such devices require that electrical signals be reliably passed between the hermetically sealed circuitry and external connectors without compromising the hermeticity of the device. Depending on the configuration of the implantable device there may be multiple electrical paths required between the device and its external connectors for delivering, for example, multi-chamber or multi-site stimulation and shock therapy, and for receiving sensed cardiac signals. These paths must be electrically and mechanically integrated with the device to provide a safe, long-term connection means, typically in the form of a component usually referred to as a header, that does not compromise the hermetic package. The header typically incorporates a plurality of receptacles for receiving the electrical connector assemblies of corresponding leads such as one or more bipolar pacing/sensing leads and/or one or more cardioverting/defibrillating leads. The receptacles contain terminal contacts electrically connected to the hermetically sealed electronic circuitry via a feedthrough assembly.

When a patient's heart does not function normally due to a genetic or acquired condition, various treatments may be prescribed to correct or compensate for the condition. Pharmaceutical therapy may be prescribed for the patient or an ICD may be implanted in the patient to administer cardiac resynchronization therapy (CRT). CRT delivers electrical impulses to the heart's two lower chambers (the ventricles) and one upper chamber (the right atrium) to improve the efficiency of each contraction of the heart and the amount of blood pumped to the body.

In conjunction with such therapy it may be desirable to continuously measure pressure in one or more chambers of the heart. For example, absolute cardiac pressure may be used as an indicator for several potentially lethal cardiac conditions. By measuring cardiac pressure, abnormal conditions may be detected and in some cases the patient's therapy may be modified to compensate for the abnormal conditions. As an example, if cardiac pressure is continuously measured, the operation of an implanted medical device such as an ICD may be adjusted as necessary according to conditions diagnosed as a result of the pressure measurements.

Conventionally, pressure sensing devices have been used to measure pressures on the right side of the heart. However, measurements of right side pressure may not provide sufficient indications for detection of conditions such as congestive heart failure, hypertension or mitral valve defects. In particular, left atrial pressure (LAP) has been identified as an excellent predictor of heart failure onset and progression. By accurately measuring LAP it becomes possible to administer preventive care before the onset of congestive heart failure thus preventing hospitalization.

Left atrial blood pressure may be measured directly in real time using a pressure sensor device incorporated into a distal end of a permanent or temporary endocardial lead. The lead is typically inserted into the right side of the heart and routed through an opening formed in a septal wall to gain access to the left side of the heart. The lead includes one or more sensors for measuring cardiac pressure on the left side of the heart and, if needed, the right side of the heart. The lead also includes an attachment structure that secures the distal end of the lead to the septal wall. The proximal end of the pressure sensing lead carries an electrical connector assembly configured to be received by a receptacle in the header of the implantable medical device which contains appropriate pressure measurement processing circuitry. For detailed descriptions of LAP measurement technology, see U.S. Pat. Nos. 6,328,699 and 6,970,742 both of which are incorporated herein in their entireties by reference.

Noninvasive telemetry has been developed allowing information such as data and control signals to be bidirectionally communicated, for example, by means of an electromagnetic energy link, between an ICD and an external system. Such an external system, typically comprising by way of example a controller, a programmer, a handheld interrogator, and/or a monitor, provides a convenient means through which the operation of the ICD may be controlled and monitored, and through which information sensed by the ICD can be read, interpreted, or otherwise used. In an electromagnetically-coupled system information is transferred from a transmitting antenna such as a telemetry coil within the ICD to a receiving antenna by way of a radiated carrier signal. The carrier signal is modulated with the data to be transmitted using an appropriate modulation scheme. The modulated carrier induces a voltage in the receiving antenna that tracks the modulated carrier signal. The received signal is then demodulated to recover the transmitted data.

The placement of a telemetry coil within a molded polymer header is known. By placing the coil outside of the hermetically sealed metal casing and within an enclosure fashioned of an electrically insulative material instead of inside the casing, the low pass filtering imparted by the casing is eliminated. Signals may thus be transmitted and received at high carrier frequencies providing high bandwitdh communication. It would be desirable to incorporate a telemetry coil within the confines of the standard, typically multiport headers of existing ICDs in an efficient, compact manner with minimal modification of the existing unit and without alteration of the external configuration of the existing header. It would also be desirable to dedicate such telemetry coil to the transmission of sensed LAP data to an external system such as a handheld interrogation unit, the ICD thus furnishing cardiac resynchronization therapy along with LAP measurement, thereby providing physicians with a powerful system to better manage the treatment of heart failure patients.

SUMMARY

In accordance with one specific, exemplary embodiment, there is provided an implantable medical device comprising a hermetically sealed casing enclosing electrical stimulation and/or sensing circuitry. A header attached to an outer surface of the casing comprises a longitudinally extending receptacle adapted to receive the electrical connector assembly of an electrical medical lead adapted to sense cardiac blood pressure. The receptacle incorporates electrical contacts disposed and configured to be engaged by corresponding electrical terminals on the electrical connector assembly. A telemetry circuit assembly is mounted vertically within the confines of the header adjacent to the receptacle. The telemetry circuit assembly comprises an electrical winding having ends electrically connected across the electrical contacts of the receptacle.

Pursuant to another specific, exemplary embodiment of the present invention, there is provided an ICD comprising a casing enclosing cardiac stimulation and sensing circuitry. A header mounted along an upper margin of the casing comprises a support carrying first and second rows of vertically spaced apart, longitudinally extending, parallel receptacles, the first and second rows of receptacles being spaced apart laterally. Each of the receptacles contains electrical contacts adapted to be engaged by corresponding electrical terminals on an associated electrical connector assembly of an electrical medical lead, one of the receptacles being adapted to receive the electrical connector assembly of a lead carrying a sensor for sensing left atrial blood pressure. A telemetry circuit assembly enclosed within the header is positioned between the first and second row of receptacles, the telemetry circuit assembly comprising an L-C resonant circuit connected to the electrical contacts of the one receptacle, whereby the circuit is operable to transmit to an external device electromagnetic signals representative of the left atrial blood pressure. In another aspect of the invention, the circuit is operable to receive from the external device electromagnetic signals for electrically powering the blood pressure sensor.

BRIEF DESCRIPTION OF THE DRAWINGS

The foregoing and other objects, features and advantages of the invention will become evident to those skilled in the art from the detailed description of the preferred embodiments, below, taken together with the accompanying drawings, in which:

FIG. 1 is a front elevation view of a multi-site ICD incorporating a header in accordance with one specific exemplary embodiment of the invention;

FIG. 2 is a side elevation view of the ICD shown in FIG. 1;

DETAILED DESCRIPTION

The following description presents preferred embodiments of the invention representing a best mode contemplated for practicing the invention. This description is not to be taken in a limiting sense but is made merely for the purpose of describing the general principles of the invention whose scope is defined by the appended claims. Although it will be evident that the invention has broad utility in that it may be used to provide electrical signals representative of fluid pressures at a wide variety of selected body sites, and may be incorporated in various lead types, including but not limited to, endocardial and epicardial leads, the invention will be described herein principally for measuring blood pressure in the left atrium of the heart.

For purposes of this description, directional terms such as "vertical", "lateral", and so forth, are used herein solely for the purpose of facilitating the description of the invention and are not to be construed as necessarily limiting the described element to a particular orientation during use.

With reference to FIGS. 1 and 2, there is shown a multi-site or multi-chamber ICD 10 incorporating a header 12 in accordance with one specific exemplary embodiment of the invention. The ICD 10 comprises a hermetically sealed metal can or casing 14 enclosing the ICD's electronic circuitry 16 with the header 12 mounted along a top margin 18 of the casing 14. The header design may be generally along the lines of those disclosed in U.S. Pat. No. 6,984,145 which is incorporated herein by reference in its entirety. The header 12 is adapted to receive the connector assemblies of a plurality of leads as will be described in greater detail below.

Figure 3:
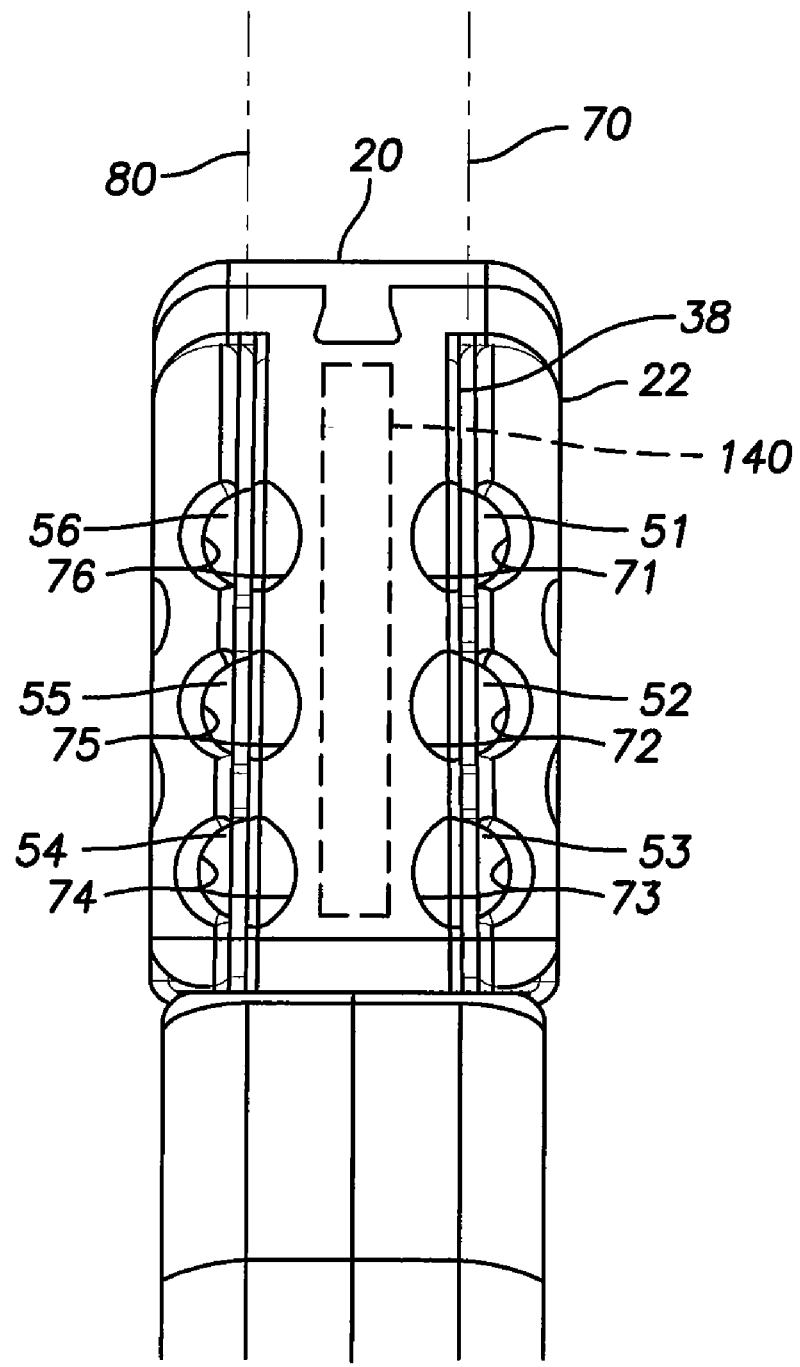
FIG. 3 is an enlargement of a portion of the front elevation view of FIG. 1.
Figure 4:
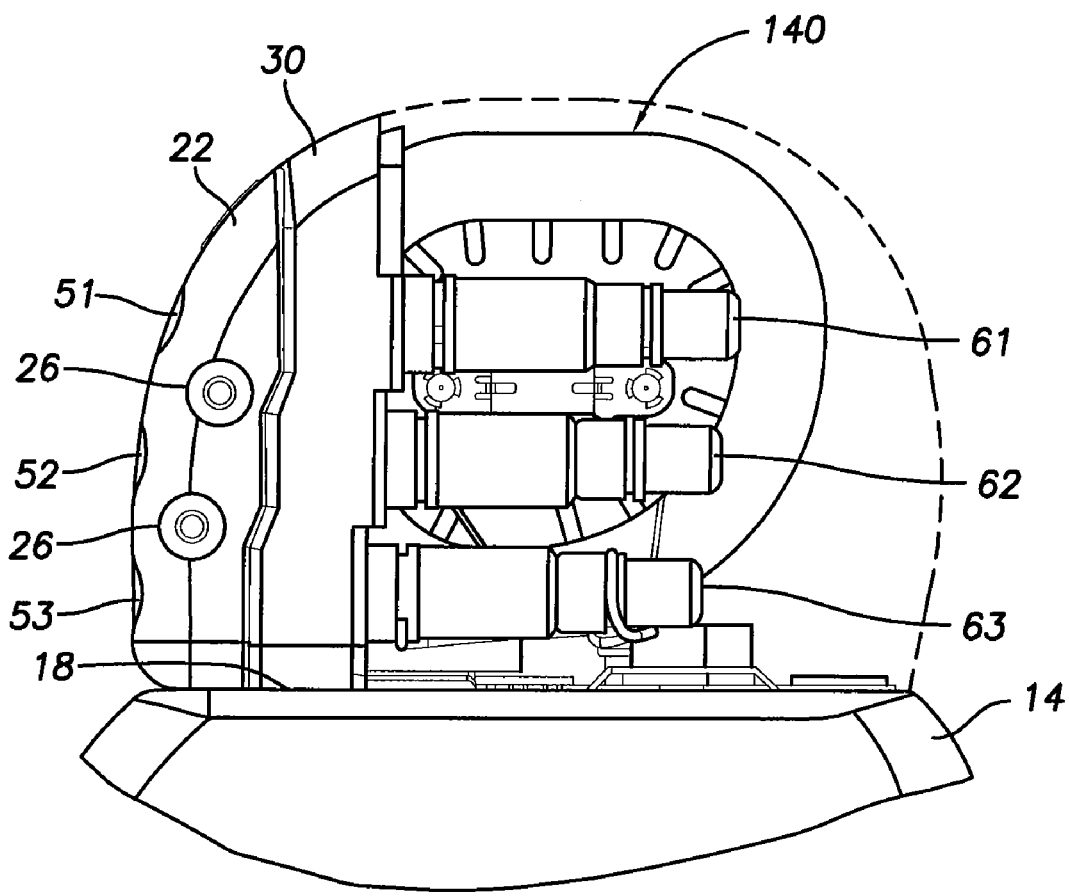
FIG. 4 is an enlarged, side elevation view of the header forming part of the ICD shown in FIGS. 1 and 2 with a portion cut away to expose certain internal components.
Figure 5:
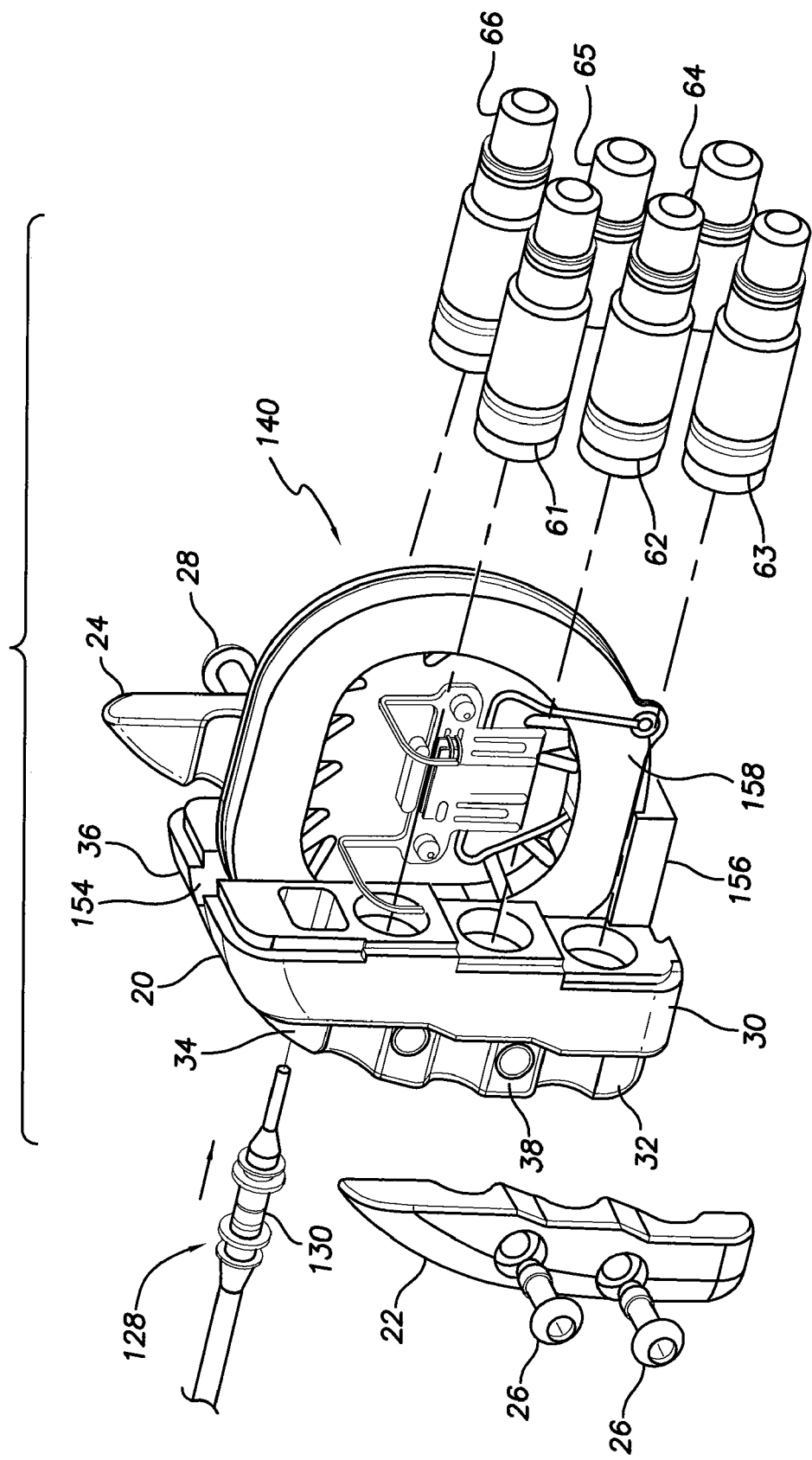
FIG. 5 is an exploded perspective view of a portion of the header of the ICD shown in the preceding figures.
Figure 6:
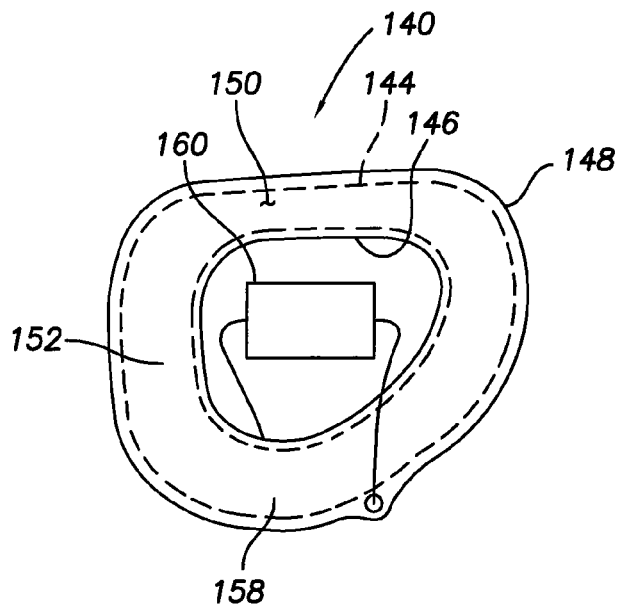
FIG. 6 is a side elevation view of a telemetry coil assembly that may be utilized in connection with an embodiment of the present invention.
Figure 7:
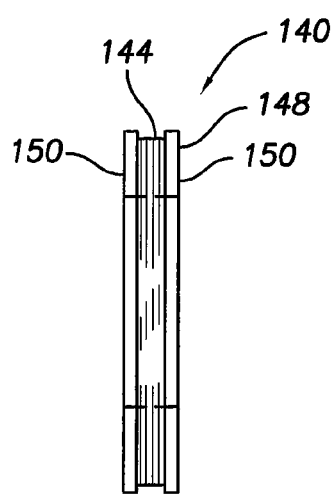
FIG. 7 is a rear elevation view of the telemetry coil assembly shown in FIG. 6.
Figure 9:
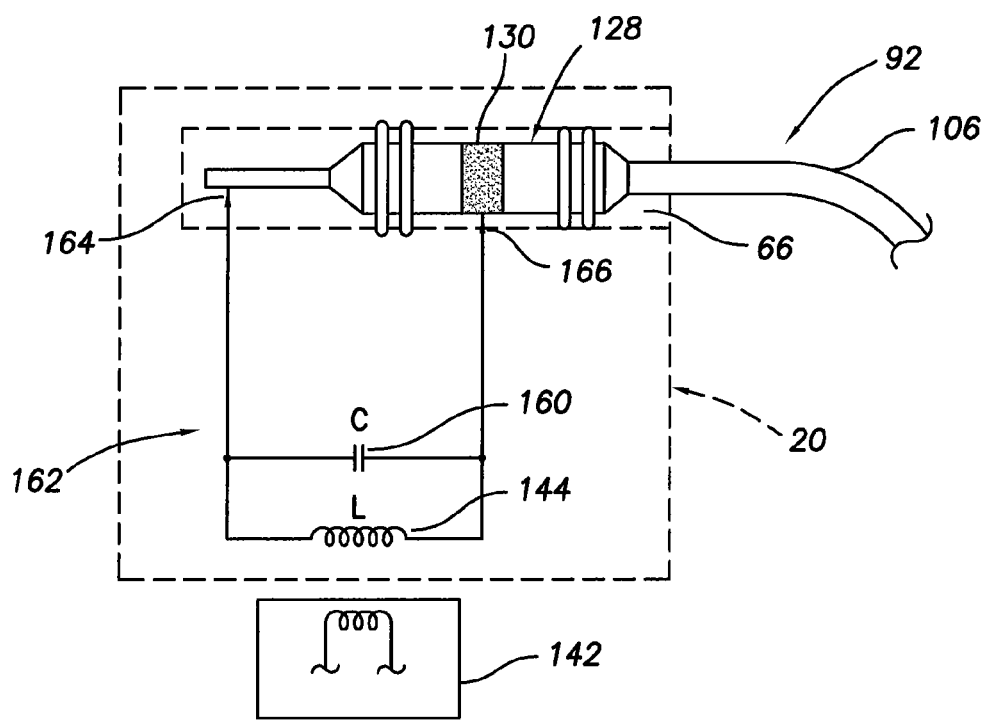
FIG. 9 is a schematic of a telemetry circuit that may be utilized in conjunction with the present invention.

With reference now also to FIGS. 3-5, the header 12 comprises a support 20, opposed side clamps 22 and 24, and side fasteners 26 and 28 for securing the side clamps 22 and 24, respectively, to the support 20 to lock the leads' connector assemblies in place. The support 20 and side clamps 22 and 24 may be fabricated of a metal such as titanium or molded of a metal such as titanium or molded of an insulative polymer such as polysulfone. The support 20 comprises a rear portion 30 and a front portion 32 narrower than the rear portion thereby defining opposed side recesses 34 and 36 for receiving the side clamps 22 and 24, respectively. The side recesses 34 and 36 comprise opposed, parallel side surfaces 38 and 40, respectively. The rear portion 30, the front portion 32 and the side clamps 22 and 24 have curved outer surfaces that form a substantially continuous, smooth, outer header surface when the side clamps are in their fully locked position, as best seen in FIGS. 1 and 2

The header 12 includes a conventional dovetail mount (not shown) on the bottom of the molded support 20 to facilitate mounting of the header on the top margin 18 of the ICD casing 14, in a manner well known in the art.

The support 20 defines a plurality (in this case six) parallel, longitudinally extending ports 51-56. Extending rearwardly from the ports 51-53 and press fit therein are receptacles 61-63, respectively, incorporating terminal contacts conforming to a standard such as the IS-1 connector standard. Extending rearwardly from the ports 54 and 55 and press fit therein are receptacles 64 and 65, respectively, incorporating terminal contacts conforming to a standard such as the DF-1 defibrillator connector standard. Thus, by way of example, the ports 51-53 may receive the connector assemblies of a right atrial bipolar pacing lead, a left ventricle bipolar pacing lead and a right ventricle bipolar pacing lead, respectively. The ports 54 and 55 may receive the electrical connector assemblies of right ventricular and superior vena cava (SVC) cardioverter/defibrillator leads, respectively. As best seen in FIG. 3, the side clamp 22 and the side surface 38 of the front portion of the support are provided with confronting longitudinally extending surfaces preferably in the form of grooves or channels 71-73 defining between them the longitudinally-extending ports 51-53. In the embodiment under consideration, the channels 71-73 may be symmetrical about a vertical interface plane 70. In similar fashion, the side clamp 24 and the side surface 40 of the front portion of the support 20 are provided with confronting longitudinally-extending grooves or channels 74-76 defining between them the longitudinally-extending ports 54-56, respectively. These channels may be symmetrical about a second vertical interface plane 80.

In a fashion well known in the art, the terminal contacts within the receptacles 71-75 are electrically connected to the pins of a feedthrough assembly (not shown) mounted in the top wall of the ICD casing 14. The pins of the feedthrough assembly are in turn coupled to the electronic circuitry 16 within the hermetically sealed casing of the ICD.

To positively lock a lead's connector assembly in place within the header 20 by means of one of the side clamps 22, 24, the associated side fasteners 26 or 28 are turned clockwise by means of a torque-limiting wrench until the torque wrench indicates audibly or otherwise that a predetermined level of torque has been applied to securely lock the lead without overtightening. In well known fashion, annular seals on the connector assemblies of the leads provide the necessary sealing against the entry of body fluids through the ports. To remove the leads, the side fasteners 26 and 28 are simply turned counterclockwise thereby releasing the side clamps 22 and 24 permitting withdrawal of the leads from the ports.

In the embodiment under consideration, the port 56 and an associated receptacle 66 are adapted to receive an IS-1 connector assembly of a left atrial pressure sensing lead that will now be described.

Figure 8:
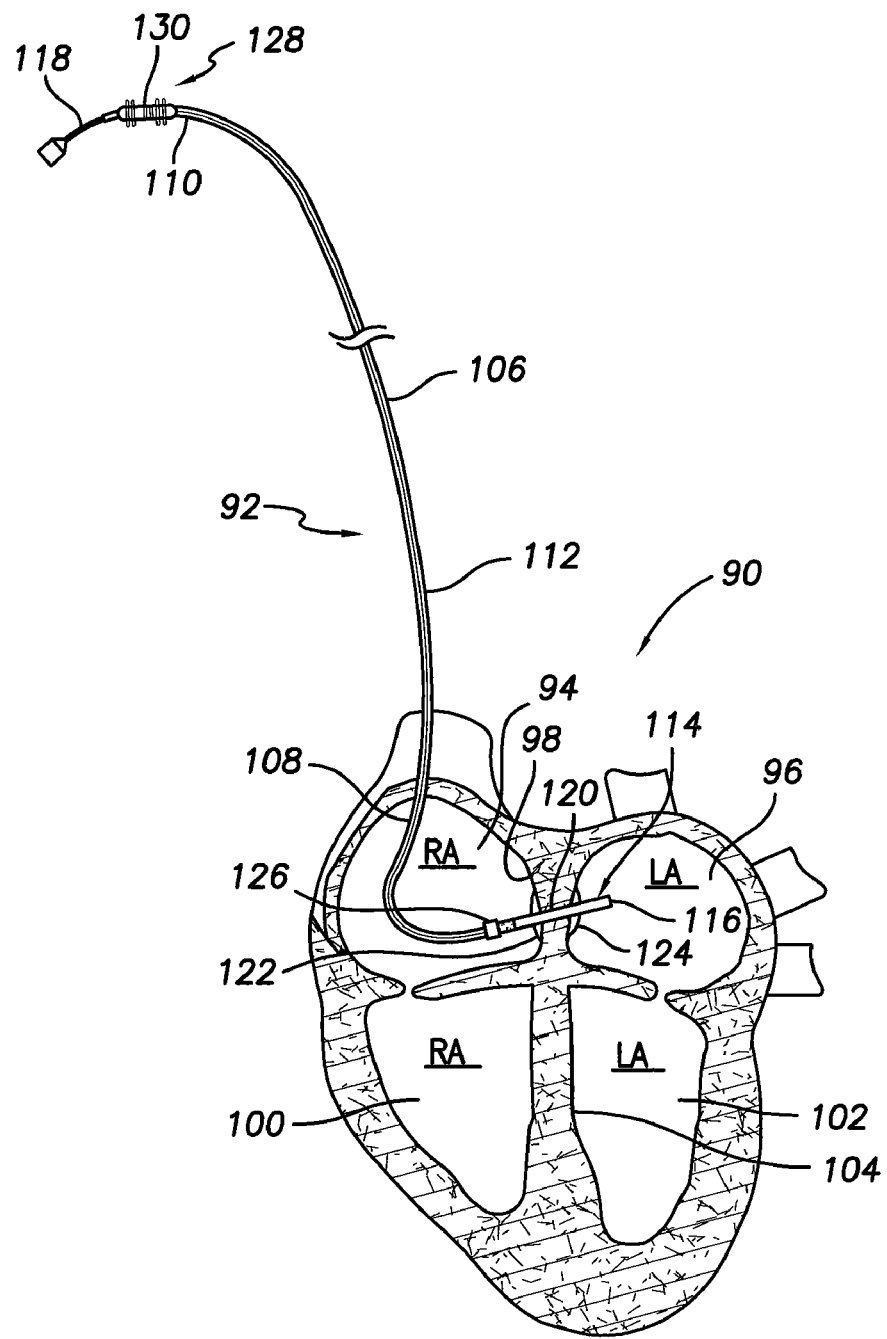
FIG. 8 is a schematic illustration of a human heart having placed therein an endocardial lead incorporating in a distal end portion thereof a left atrial pressure sensor module.

FIG. 8 schematically depicts a human heart 90 having placed therein a left atrial blood pressure measuring lead 92. The heart comprises right and left atrial chambers 94 and 96, respectively, separated by an atrial septum 98, and right and left ventricular chambers 100 and 102, respectively, separated by a ventricular septum 104. The lead 92, shown implanted, by way of example, through the atrial septum 98, includes a lead body 106 having a distal end portion 108 and a proximal end 110. The lead body 106 further comprises a sheath 112 made of a biostable, biocompatible insulating material such as silicone rubber or polyurethane. The sheath 112 may comprise a conventional multilumen structure enclosing one or more electrical conductors, and may include fluid carrying lumens and/or other components (not shown). In the specific, exemplary embodiment of FIG. 8, the distal end portion 108 of the lead body encloses a pressure sensor module 114 adjacent to a distal tip 116 of the lead body. The pressure sensor module 114 may be entirely or partially positioned in the left atrium 96 when the lead 92 is placed or implanted so as to monitor the pressure therein.

The distal end portion 108 of the lead body 106 may be initially introduced into the heart via the right atrium 94 using known techniques. For example, a stylet 118 inserted into a lumen of the lead body may be used to manipulate and steer the distal end portion 108 of the lead body to a target location.

To pass the distal end portion 108 of the lead body 106 from the right atrium through to the left atrium, the atrial septum may be pierced using, for example, a piercing tool (not shown) or using a lead body having a relatively sharp and hard distal tip (not shown). In either case, the piercing device is manipulated to create an access tunnel 120 through the septum. The access tunnel may be made in the region of the fossa ovalis since this is typically the thinnest portion of the atrial septum. By appropriately manipulating the stylet, the distal end portion 108 of the lead body 106 is then maneuvered through the access tunnel in the atrial septum so that all or a portion of the pressure sensing module 114 protrudes into the left atrium 96.

The distal end portion 108 of the lead body includes an attachment structure serving to attach the lead to the atrial septum 98. The attachment structure may take many forms including, without limitation, one or more tines, flexible membranes, inflatable membranes, circumferential tines and/or distal end lead body portions having a J-shaped configuration. FIG. 8 represents the attachment structure in a generalized manner including first and second structures 122 and 124 on opposite sides of the septum 98.

The distal end portion 108 of the lead body may also carry one or more electrodes such as a ring electrode 126 disposed in the right atrium 94 proximally of the pressure sensor module for unipolar pacing and/or sensing the right atrium. Additional electrodes (not shown) may be carried by the distal end portion of the lead body so as to provide bipolar pacing, sensing and/or shocking operation, in accordance with structures and techniques well-known in the art.

Attached to the proximal end of the lead body is an electrical connector assembly 128 adapted to be received by the port 56 and associated receptacle 66 in the header 20 of the ICD 10 which contains appropriate pressure measurement processing circuitry as well as pacing, sensing, shocking and other electrical circuitry all in accordance with techniques and principles well-known in the art.

The connector assembly 128 carries a plurality of terminal contacts, represented by the ring contact 130, electrically connected by conductors to the pressure sensor module and to any electrode(s) disposed along the distal end portion of the lead body. The electrical conductors may comprise conventional coil or cable conductors or a combination of both; to minimize the diameter of the lead body, cable conductors are preferred.

With reference to FIGS. 4-7 and 9, a telemetry circuit assembly 140 is enclosed within the header 20 of the ICD 10. The telemetry circuit of the assembly 140 may be selectively coupled to an external device such as, for example, a hand held interrogator 142 by means of an appropriate electromagnetic energy link. Sensed LAP measurements may thereby be transmitted to the external device 142. In well known fashion, the external device may be used also to power the circuitry of the pressure sensor module 114 by way of the telemetry link so that the telemetry circuit assembly 140 serves a dual purpose.

The telemetry circuit assembly 140 comprises a multi-turn winding or coil 144 wound about an inner wall 146 of a generally toroidal shaped frame 148 having vertical, planar side walls 150 confining the coil 144. The telemetry circuit assembly 140 has a front, generally vertical leg 152 received within a vertical groove 154 formed in a rear surface of the support 20 between the spaced apart rows of receptacles 61-63 and 64-66. The assembly 140 may be further constrained against lateral displacement by a channel 156 projecting rearwardly from the lower part of the support 20 and within which a lower leg 158 of the circuit assembly 140 is received.

A capacitor 160 is connected across the winding 144 of the telemetry circuit assembly 140 to form an L-C resonant circuit 162. The capacitor 160 is preferably disposed within the confines of the generally toroidal frame 148. The L-C resonant circuit 162 is connected across the contacts 164 and 166 of the LAP. lead Although in the embodiment shown six receptacles are illustrated in two vertical rows of three receptacles each, it will be evident that the unit may incorporate a greater or lesser number of receptacles. Thus, for example, only a single receptacle, positioned to one side or the other of the preferably vertically oriented telemetry coil assembly 140 may be provided in which case, the receptacle may be dedicated to providing left atrial pressure measurements to an external system.

While certain exemplary embodiments have been described above in detail and shown in the accompanying drawings, it is to be understood that such embodiments are merely illustrative and not restrictive of the invention. In particular, it should be recognized that the teachings of the invention apply to a wide variety of systems and processes and it will be recognized that various modifications may be made to the illustrated and described embodiments without departing from the broad inventive scope thereof. Accordingly, the invention is intended to cover any changes, adaptations or modifications that are within the scope and spirit of the invention as defined by the appended claims.

What is claimed is:

1. An implantable medical device comprising:
a hermetically sealed casing enclosing electrical stimulation and/or sensing circuitry;
a header attached to an outer surface of said casing, the header comprising a longitudinally extending receptacle adapted to receive the electrical connector assembly of an electrical medical lead adapted to sense cardiac blood pressure, said receptacle incorporating electrical contacts disposed and configured to be engaged by corresponding electrical terminals on said electrical connector assembly; and
a telemetry circuit assembly mounted vertically within the confines of the header adjacent to said receptacle, said telemetry circuit assembly comprising an electrical winding having ends electrically connected across the electrical contacts of said receptacle.

2. The device of claim 1 wherein:
the header comprises a support having a rear surface defining a vertical groove adjacent to said receptacle for receiving a portion of said telemetry circuit assembly.

3. The device of claim 1 wherein the device further comprises:
a capacitor electrically connected across the winding of the telemetry circuit assembly.

4. An implantable cardiac defibrillator (ICD) comprising:
a casing enclosing cardiac stimulation and sensing circuitry;
a header mounted along an upper margin of said casing, the header comprising a support carrying first and second rows of vertically spaced apart, longitudinally extending, parallel receptacles, said first and second rows of receptacles being spaced apart laterally, each of said receptacles containing electrical contacts adapted to be engaged by corresponding electrical terminals on an associated electrical connector assembly of an electrical medical lead, one of said receptacles being adapted to receive the electrical connector assembly of a lead carrying a sensor for sensing left atrial blood pressure; and
a telemetry circuit assembly enclosed within said header, said telemetry circuit assembly being positioned between said first and second row of receptacles, said telemetry circuit assembly comprising an L-C resonant circuit connected to the electrical contacts of said one receptacle, whereby said circuit is operable to transmit to an external device electromagnetic signals representative of said left atrial blood pressure.

5. The ICD of claim 4 wherein:
at least one of said receptacles is adapted to receive the connector assembly of a cardiac pacing and/or sensing lead.

6. The ICD of claim 4 wherein:
at least one of said receptacles is adapted to receive the connector assembly of a cardioverting/defibrillation lead.

7. The ICD of claim 4 wherein:
the telemetry circuit assembly comprises a frame, a portion of said frame being received within a vertical groove defined by said support and disposed between said laterally spaced apart rows of receptacles.

8. The ICD of claim 7 wherein:
the frame comprises a generally toroidal structure carrying a wound wire coil and a capacitor connected across said coil, said capacitor being positioned within the confines of said generally toroidal frame structure.

9. The ICD of claim 4 wherein:
the support further includes clamps for securing the electrical medical leads in place within corresponding ports defined by said support.

10. The ICD of claim 4 wherein:
said circuit is operable to receive from said external device electromagnetic signals for electrically powering said left atrial blood pressure sensor.

11. An implantable medical device comprising:
a hermetically sealed casing enclosing electrical stimulation and/or sensing circuitry;
a header attached to an outer surface of said casing, the header comprising at least two parallel, longitudinally extending, laterally spaced apart receptacles each adapted to receive an electrical connector assembly at a proximal end of an electrical medical lead, each of said receptacles incorporating electrical contacts disposed and configured to be engaged by corresponding electrical terminals on an associated electrical connector assembly; and
a telemetry circuit assembly contained within the confines of the header, the telemetry circuit assembly being mounted within the space separating said at least two receptacles, said telemetry circuit assembly comprising an electrical winding having ends electrically connected across the electrical contacts of one of said at least two receptacles.

12. The device of claim 11, wherein:
said one of said at least two receptacles is adapted to receive the electrical connector assembly of a cardiac blood pressure sensing lead.

13. The device of claim 11, wherein:
said one of said at least two receptacles is adapted to receive the electrical connector assembly of a left atrial blood pressure sensing lead.

14. The device of claim 11 wherein:
the header comprises a support having a rear surface defining a groove between said receptacles for receiving said telemetry circuit assembly.

15. The device of claim 11 wherein the device further comprises:
a capacitor electrically connected across the winding of the telemetry circuit assembly.

* * * * *

UNITED STATES PATENT AND TRADEMARK OFFICE
CERTIFICATE OF CORRECTION

PATENT NO. : 7,650,191 B1  Page 1 of 1
APPLICATION NO. : 11/623394
DATED : January 19, 2010
INVENTOR(S) : Lim et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 553 days.

Signed and Sealed this

Twenty-third Day of November, 2010

David J. Kappos
*Director of the United States Patent and Trademark Office*